(12) United States Patent
Kressner et al.

(10) Patent No.: US 7,774,885 B2
(45) Date of Patent: Aug. 17, 2010

(54) BRUSH HEAD FOR A TOOTHBRUSH

(75) Inventors: Gerhard Kressner, Altenstadt (DE); Michael Stolper, Eschborn (DE)

(73) Assignee: Braun GmbH, Kronberg (DE)

( * ) Notice: Subject to any disclaimer, the term of this patent is extended or adjusted under 35 U.S.C. 154(b) by 1638 days.

(21) Appl. No.: 10/501,851

(22) PCT Filed: Nov. 19, 2002

(86) PCT No.: PCT/EP02/12935

§ 371 (c)(1),
(2), (4) Date: Oct. 25, 2004

(87) PCT Pub. No.: WO03/071979

PCT Pub. Date: Sep. 4, 2003

(65) Prior Publication Data

US 2005/0039276 A1 Feb. 24, 2005

(30) Foreign Application Priority Data

Feb. 27, 2002 (DE) ................. 102 08 528

(51) Int. Cl.
*A61C 17/22* (2006.01)

(52) U.S. Cl. .............. 15/22.1; 15/28; 15/22.4

(58) Field of Classification Search .......... 15/22.1, 15/22.2, 22.4, 28
See application file for complete search history.

(56) References Cited

U.S. PATENT DOCUMENTS

| | | |
|---|---|---|
| 2,140,307 A | 12/1938 | Alfred et al. |
| 2,306,264 A | 12/1942 | Hart |
| 5,398,366 A | 3/1995 | Bradley |
| 5,435,032 A | 7/1995 | McDougall |
| 5,467,495 A | 11/1995 | Boland et al. |
| 5,500,970 A | 3/1996 | Maurer et al. |
| 5,524,312 A | 6/1996 | Tan et al. |
| 5,528,786 A | 6/1996 | Porat et al. |
| 5,732,433 A * | 3/1998 | Gocking et al. ........... 15/28 |
| 5,836,030 A * | 11/1998 | Hazeu et al. ........... 15/22.1 |
| 5,842,244 A | 12/1998 | Hilfinger et al. |
| 6,000,083 A | 12/1999 | Blaustein et al. |
| 6,021,538 A | 2/2000 | Kressner et al. |
| 6,367,108 B1 | 4/2002 | Fritsch et al. |
| 6,438,786 B2 | 8/2002 | Harada |
| 6,510,575 B2 | 1/2003 | Calabrese |
| 6,574,820 B1 | 6/2003 | DePuydt et al. |
| 6,735,803 B2 | 5/2004 | Kuo |
| 6,760,946 B2 * | 7/2004 | DePuydt ................ 15/22.4 |
| 7,219,384 B2 * | 5/2007 | Hohlbein ............... 15/22.1 |
| 7,392,562 B2 | 7/2008 | Boland et al. |
| 2003/0154568 A1 * | 8/2003 | Boland et al. ............ 15/28 |

(Continued)

FOREIGN PATENT DOCUMENTS

DE 94 11 158 9/1995

(Continued)

*Primary Examiner*—Lee D Wilson
(74) *Attorney, Agent, or Firm*—John P. Colbert (57) ABSTRACT

A toothbrush head has several bristle support segments movable relative to each other, and driving elements that change the position of the bristle support segments relative to each other. The driving elements have a cam control surface that causes the individual bristle support segments to execute an additional movement superposed upon the movement of the bristle support.

29 Claims, 7 Drawing Sheets

U.S. PATENT DOCUMENTS

2005/0039276 A1 * 2/2005 Kressner et al. .............. 15/22.1

FOREIGN PATENT DOCUMENTS

| DE | 296 00 236 | 4/1996 |
| --- | --- | --- |
| DE | 297 05 182 | 7/1997 |
| DE | 198 57 032 | 7/1999 |
| DE | 198 31 412 | 1/2000 |
| DE | 6905 11 398 | 2/2000 |
| EP | 0 901 329 | 4/1997 |
| EP | 10 835 081 | 11/1999 |
| EP | 1 093 770 | 4/2001 |
| EP | 0 765 642 | 2/2002 |
| WO | WO96/02165 | 2/1996 |
| WO | WO97/41753 | 11/1997 |
| WO | WO01/43586 | 6/2001 |

* cited by examiner

BRUSH HEAD FOR A TOOTHBRUSH

BACKGROUND

This invention relates to a brush head for a toothbrush, which includes a hand-piece with a drive mechanism for the brush head, with an in particular disk- or plate-shaped bristle support which carries an array of bristles, is mounted for movement on a brush head support and includes connecting elements for coupling to the drive mechanism in the hand-piece of the toothbrush, said bristle support being divided into several bristle support segments movable relative to each other, and with driving elements changing the position of the bristle support segments relative to each other in dependence upon the position of the entire bristle support.

In electric toothbrushes increased importance has been recently attached to the cleaning of interproximal spaces and periodontal pockets. Attempts are made to work the bristles into the interproximal spaces to remove plaque buildup there. However, the length and the fixed securing of the bristles set a certain limit to these attempts. From EP 0 835 081 B1 a brush section for an electric toothbrush is known, which includes a bristle support which is rotary about an axis of rotation perpendicular to the brush longitudinal direction and is adapted to be driven in an oscillatory rotary movement. Arranged in several rings on the bristle support are bristle tufts, some of the bristle tufts being provided on the outermost bristle tuft ring in diametrically opposed segments, said tufts protruding beyond the remainder of the bristle tufts and being of increased stiffness. These tufts, referred to as power tips, are intended to penetrate in the interproximal spaces to perform a particularly thorough cleaning function there. This prior known arrangement is however capable of further improvement. Owing to the oscillation of the bristle support the power tips perform a wiping action into and out of the interproximal spaces, without however optimally reaching the respective interproximal space due to the motion curve resulting in the process, because it is first necessary to wipe over the gums before the interproximal space can be entered. Furthermore, the penetration depth of the power tips in the inter-proximal space amounts to no more than the amount of protrusion over the remainder of the bristles.

From U.S. Pat. No. 5,732,433 a brush head of an electric toothbrush is known, which includes another bristle support with supplementary bristles in addition to the main bristle support driven in an oscillatory rotational pattern about an axis of rotation normal to the brush longitudinal direction and carrying an approximately circular array of bristles. This additional bristle support is constructed as a component separate from the main bristle support and sits directly on a drive shaft extending in the interior of the brush head support and driving also the main bristle support. The additional bristles are driven to oscillate in a rotary manner about the drive axis, that is, about the longitudinal axis of the brush, and are to sweep out the interproximal spaces. Apart from the fact that this separate drive of the supplementary bristle array is relatively complex, the aforementioned problem is not eliminated, that is, the extended additional bristles are unable to penetrate between adjacent teeth sufficiently deeply.

In this context, an improvement is achievable by enabling the power tips to penetrate in the interproximal space in a pulsing motion. EP 1 093 770 A2 proposes a brush head of the prior-art type in which the essentially disk-shaped bristle support, which is adapted to be driven in rotary oscillatory manner, is divided into several bristle support segments that are movable relative to each other. The power tips are arranged on a rocker which is mounted for rocking motion about a rocker axis extending in a direction transverse to the axis of rotation of the bristle support and forms opposite segments of the bristle support, so that by rocking up and down corresponding pulsing or poking motions of the power tips can be achieved. In this arrangement the rocking motions are produced by a crank mechanism mounted on the drive shaft provided in the interior of the brush tube to effect the oscillatory rotational motion of the bristle support. Accordingly, the rocking motion is coupled to the oscillatory rotational motion of the bristle support, that is, the rocker-like bristle support segments are moved in dependence upon the rotary position of the entire bristle support. Due to the arrangement of the power tips on a rocker, however, only those power tips that are arranged on one side will enter the interproximal space at a time, because the opposite power tips are withdrawn according to the principle of a seesaw. Moreover, the drive mechanism producing the rocking motion is relatively complex in addition to necessitating a special type of bristle support drive, namely a drive shaft rotating or oscillating about its longitudinal axis.

SUMMARY

According to one aspect of the invention, the driving elements causing relative movement of the bristle support segments comprise a cam control surface as well as an engagement element cooperating therewith, which are provided on the brush head support and at least one bristle support segment in order to move this at least one bristle support segment correspondingly when the bristle support moves about its axis of motion. For achieving the desired motion of the bristle support segment, it is thus not necessary to provide an elaborate crank mechanism mounted on the shaft. By providing a cam surface, the basic movement of the entire bristle support relative to the brush head support is utilized for additionally driving individual bristle support segments, so that these individual bristle support segments execute an additional movement that is superposed upon the basic movement of the bristle support. Crankpins with weld-on tappets can be omitted.

According to the invention the driving elements causing relative movement of the bristle support segments comprise a cam control surface as well as an engagement element cooperating therewith, which are provided on the brush head support and at least one bristle support segment in order to move this at least one bristle support segment correspondingly when the bristle support moves about its axis of motion. For achieving the desired motion of the bristle support segment, it is thus not necessary to provide an elaborate crank mechanism mounted on the shaft. By providing a cam surface, the basic movement of the entire bristle support relative to the brush head support is utilized for additionally driving individual bristle support segments, so that these individual bristle support segments execute an additional movement that is superposed upon the basic movement of the bristle support. Crankpins with weld-on tappets can be omitted.

It will be understood that the basic movement of the bristle support may be embodied in different ways. Possible are, for example, translational movements. In particular however the bristle support is caused to oscillate rotationally about an axis of rotation extending essentially perpendicular to the longitudinal direction of the brush head. With this construction, the cam control surface extends on an arc about the axis of rotation of the bristle support so that the at least one movable bristle support segment is driven in accordance with the rotary movement of the bristle support.

The cam control surface may be formed or arranged on the bristle support segment itself while the cooperating engagement element is formed fast with the brush head support. In an advantageous further aspect of the invention provision is however made for the cam control surface to be formed fast with the brush head support while the cooperating engagement element is disposed on the bristle support segment to be moved. The cam control surface and the engagement element cooperating therewith may be formed directly by surfaces of the brush head support and, respectively, the respective bristle support segment. The cam control surface and/or the cooperating engagement element may also be constructed as separate elements secured to the respective bristle support segment and, respectively, the brush head support. This enables them to be constructed in particularly wear-resistant and/or replaceable manner.

In some embodiments, the bristle support possesses at least one rigid bristle support segment that executes only the rotary movement or basic movement, as well as at least one movable bristle support segment that executes the basic movement plus a poking movement. In a further aspect of the invention it is also possible for several bristle support segments, preferably one pair of bristle support segments arranged at diametrically opposite sides on the bristle support, to be movably mounted and to be driven by the cam control in dependence upon the rotary position of the bristle support. With this construction, the corresponding cam control surface may include several sections, whereof a respective one of said sections is associated with one of the driven bristle support segments.

The cam control may be configured in a variety of ways. In one preferred configuration of the invention the cam control is constructed as a positive control, such that the bristle support segments driven by it are positively controlled in both the one and the other direction. The corresponding cam control surface and the engagement element cooperating therewith are always in relative engagement and act in opposed directions of movement. The engagement element cooperating with the cam control surface can not be lifted clear of the cam control surface, being constrained to follow its movement. Such a positive control may be realized, for example, by providing for the engagement element to run in a cam control groove, providing, so to speak, two parallel cam control surfaces between which the engagement element runs. A positive control may also be provided in that the engagement element associated with the cam control surface forms a curved engagement surface that is curved in the same direction and with about the same curvature radius as the cam control surface, so that a concave surface sits with exact fit on a convex surface. When the corresponding bristle support segment is mounted for movement about an axis parallel to the axis of curvature of the two engagement surfaces, a movement of the bristle support segment in a direction transverse to its movable bearing axis results in a positively defined swivel position.

In an alternative further aspect of the invention the cam control may also be of the type that is not positively controlled. The respective bristle support segment may be mounted in such fashion that the cam control surface and the engagement element cooperating therewith can be lifted clear of each other, enabling disengagement of the cam control. In practice, however, this is prevented from occurring because the reaction forces acting on the bristles during brushing urge the bristle support segment downwards, hence pressing the cam control surface and the engagement element into relative engagement. Accordingly, it is not necessary for the cam drive to be designed to act in both directions, instead it is sufficient for it to effect movement of the bristle support segment into only one direction. As the case may be, provision may also be made for a biasing or spring device that counteracts a lift-off movement of the engagement element from the cam control surface.

In another aspect of the invention the cam control is configured in such manner that the bristle support segments driven by the cam control execute poking movements essentially in the bristles' longitudinal direction. In other words, the bristle support is rotated in its entirety about an axis of rotation essentially parallel to the main direction of the bristled area. In addition, a poking motion is superposed upon one or several bristled segments.

In a further aspect of the invention the cam control is configured such that a maximum stroke, that is, the maximum poking movement of the movable bristle support segments occurs when the bristle support is in its neutral mid-position from which it is drivable in oscillatory manner in opposite directions. Each time the bristle support passes through zero the bristle support segments driven by the cam control experience a maximum up-stroke. By contrast, with the displacement of the bristle support at its maximum, the movable bristle support segments assume a minimum stroke position or a retracted position.

Depending on the configuration of the bristled area and the arrangement of the power tips, with the displacement of the bristle support at its maximum provision may also be made for the movable bristle support segments to occupy a maximum stroke position while the movable bristle support segments assume their retracted, minimum stroke position when the bristle support passes through zero.

In the event of several bristle support segments being driven by the cam control, the bristle support segments are preferably raised or lowered in the same timed sequence, that is, raising takes place in concert, and so does lowering.

The movable bristle support segments driven by the cam control may be mounted on the immovable part of the bristle support or a bristle support base in a variety of ways. Provision may be made for the movable bristle support segments to be mounted for translational movement, being in particular displaceable in the direction of the axis of rotation of the bristle support. This enables a poking movement to be accomplished exactly parallel to the direction of rotation of the bristle support. In a further aspect of the invention however provision is preferably made for mounting the movable bristle support segments for swivel movement, in particular about a swivel axis extending in a direction transverse to the axis of rotation of the bristle support. Owing to the arrangement of the swivel axis, it is possible to determine, in addition to the cam control surface design, the height and the track curve of the movement of the respective bristle support segment, which is produced by the cam control.

According to a first preferred embodiment of the invention the movable bristle support segments sit on a radially extending swivel axis in such manner that bristles sitting on the bristle support segment swivel in a plane tangential to the circumferential direction of the bristle support. By virtue of the cam control, the bristles sitting on the movable bristle support segment hence experience a wagging motion in the circumferential direction. As this occurs, the bristle tufts spaced from the swivel axis poke in their longitudinal direction.

According to a second preferred embodiment of the invention the movable bristle support segments are each adapted to swivel about a transverse axis that extends in a direction transverse to the axis of rotation of the bristle support and lies in the plane defined by the bristle support, such that bristles sitting on the respective movable bristle support segment perform a rocking motion in a plane radial to the axis of rotation of the bristle support. In cases where movable bristle support segments are arranged at diametrically opposite sides, the bristles disposed thereon thus perform a swivel movement towards each other, with the bristles spaced from the swivel axis experiencing a stroke motion. It will be understood, of course, that the bristle support segments may be caused to swivel about separate, preferably parallel, axes. It is also possible for the bristle support segments to be mounted on a common swivel axis.

Conveniently, the movable bristle support segments mount a particular type of bristle. In particular the bristles arranged on the movable bristle support segments protrude beyond the bristles arranged on the fixed bristle support segment in the bristles' longitudinal direction. Alternatively or additionally, the bristles protruding in longitudinal direction may be of greater stiffness than the remainder of the bristles. In particular the bristle tufts arranged on the movable bristle support segments form so-called power tips.

The movable bristle support segments lie preferably in a radially outer zone of the bristle support, forming in particular a segment of the radially outer periphery of the bristle support. Bristles arranged in a radially outer zone of the respective bristle support segment may be longer and/or stiffer than bristles arranged in a radially inner zone. The radially outer bristles may also fulfill special functions as, for example, a wear indicating function.

Further objects, advantages, features and application possibilities of the present invention will become apparent from the subsequent description of preferred embodiments illustrated in the accompanying drawings.

DETAILED DESCRIPTION

Figure 1:
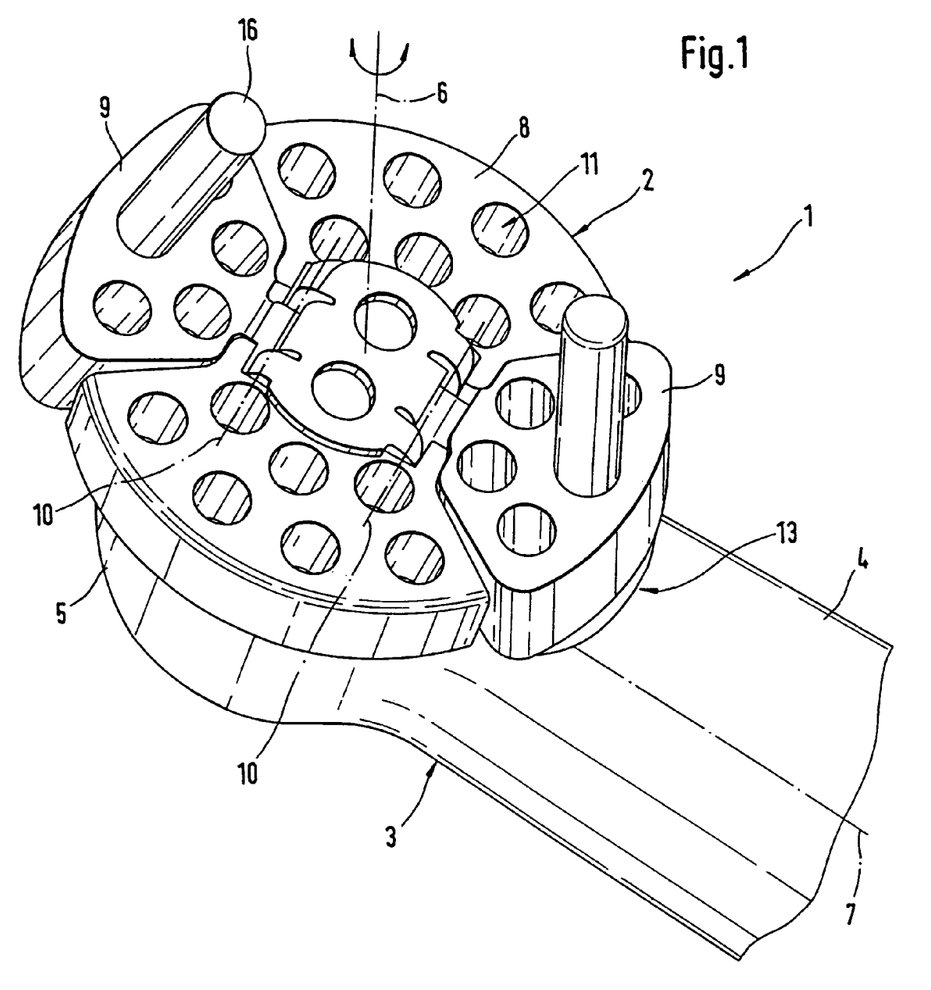
FIG. 1 is a perspective view of a brush head of an electric toothbrush having a disk-shaped bristle support that is adapted to be driven in an oscillatory rotating manner and includes two movably mounted bristle support segments adapted to swivel about transverse axes.
Figure 2:
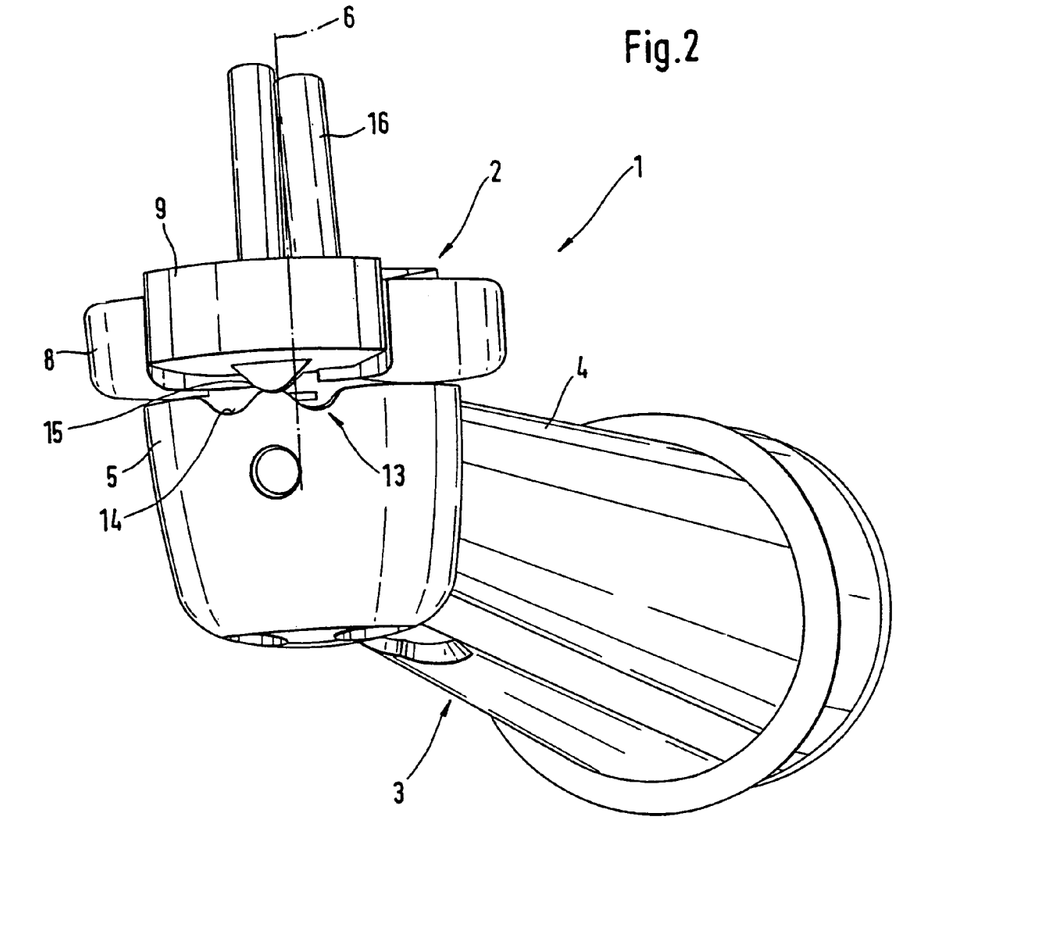
FIG. 2 is a perspective view of the brush head of FIG. 1 as seen looking from below at an angle, showing a cam control of the movably mounted bristle support segments.

The brush head 1 illustrated in FIGS. 1 and 2 has an essentially disk- or plate-shaped bristle support 2 mounted on a brush head support 3. The brush head support 3 is constructed as a brush tube 4 providing a bristle support mounting structure 5 in the region of the bristle support 2.

The bristle support 2 is mounted for rotation about an axis of rotation 6 extending essentially perpendicular to the plane defined by the bristle support 2 and also essentially perpendicular to the longitudinal direction of the brush head 1, and is adapted to be driven in an oscillatory rotating manner. To accomplish this, provision is made in the interior of the brush tube 4 for a driving element 7 that is adapted to be coupled to a drive mechanism of a handpiece of a toothbrush, not shown in more detail, when the brush head 1 is attached to the toothbrush handpiece, and is connected to the bristle support 2 by gearing not shown in greater detail.

The bristle support 2 is rotatable from the neutral basic position shown in FIG. 1 in either direction of rotation. The angle of oscillation may be less than ±45°, for example, in particular about ±35°.

As FIG. 1 shows, the bristle support 2 comprises a rigid bristle support segment 8 and two bristle support segments 9 movable relative thereto which, roughly speaking, are shaped in an approximately wedge-shaped configuration and combine with the rigid bristle support segment 8 to form an approximately circular disk.

The two movable bristle support segments 9 are arranged opposite to one another, lying approximately on the longitudinal axis of the brush head 1 in the non-displaced position of the bristle support 2 shown in FIG. 1. The two bristle support segments 9 are each mounted for swivel movement about a respective transverse axis 10 extending in the plane defined by the bristle support 2 as well as in a direction transverse to the axis of rotation 6 and transverse to the longitudinal direction of the brush head 1. The two parallel transverse axes 10 are close to the center of the bristle support 2, being however spaced a small distance from the axis of rotation 6 in the embodiment shown.

In a non-displaced position the two movable bristle support segments 9 lie essentially in the plane defined by the rigid bristle support segment 8. They can be lifted in upward direction, that is, toward the side carrying the array of bristles 11, swiveling about their respective transverse axes 10 so that the bristle tufts 12 arranged on the respective bristle support segment 9 execute a poking motion. It will be understood, of course, that both the bristle support segments 9 and the rigid bristle support segment 8 rotate with the bristle support 2 about the axis of rotation 6.

The two movable bristle support segments 9 are driven in dependence upon the rotary position of the bristle support 2 relative to the brush head support 3. As FIG. 2 shows, provision is made for a cam control 13 for raising and lowering the movable bristle support segments 9 with a corresponding rotation of the bristle support 2 about the axis of rotation 6. The cam control 13 comprises a cam control surface 14 provided on the brush head support 3 in a section of the brush head support 3 lying underneath the bristle support 2. As FIGS. 1 and 2 show, the cam control surface 14 includes two sections lying each under one of the two movable bristle support segments 9. The section of the cam control surface 14 shown in FIG. 2 is formed in the bristle support mounting structure 5 situated at the forward end of the brush head support 3. The second section of the cam control surface 14 is likewise formed on the bristle support mounting structure 5, yet in its region adjoining the brush tube 4.

The cam control surface 14 extends in an arc about the axis of rotation 6. It lies in the area of the longitudinal plane of symmetry of the brush tube. As FIG. 2 shows, the cam control surface 14 is in particular symmetrical to the longitudinal plane of symmetry of the brush head in which the axis of rotation 6 lies. It comprises a centrally located protuberance and two depressions adjoining the protuberance to the right and left (cf. FIG. 2).

Cooperating with the cam control surface 14 is an engagement element 15 arranged on the movable bristle support segment 9, particularly on its side close to the brush head support 3. As FIG. 2 shows, the engagement element 15 may be a downwardly protruding engagement nose sliding along the cam control surface 14 and having a contour corresponding approximately to the two depressions of the cam control surface 14.

When the bristle support 2 rotates about the axis of rotation 6, the engagement elements 15 on the two bristle support segments 9 slide along their respective cam control surface 14 on the brush head support 3. This causes the radially outer peripheries of the bristle support segments 9 to be raised or lowered, that is, the respective bristle support segment 9 swivels about its swivel axis 10. The cam control surface 14 is formed such that the maximum stroke position of the bristle support segments 9 is reached when the bristle support 2 passes through zero, meaning that is passes the non-displaced position shown in FIGS. 1 and 2. When the bristle support 2 reaches its maximum displacement position of its oscillating rotation, the engagement elements 15 enter the depressions of the cam control surface 14, causing the bristle support segments 9 to be in their lowered position in which they lie approximately in the plane of the rigid bristle support segment 8.

Provision may be made for a biasing device, not shown in more detail, which urges the cam control 13 into its engaged position. For example, a spring device may urge the two bristle support segments 9 downwards against the brush head support 3 so that the engagement elements 15 rest on the cam control surface 14. It will be understood, however, that such a biasing device may also be dispensed with. The bristle support segments 9 are urged against the cam control surface 14 by the reaction forces produced while brushing.

Figure 3:
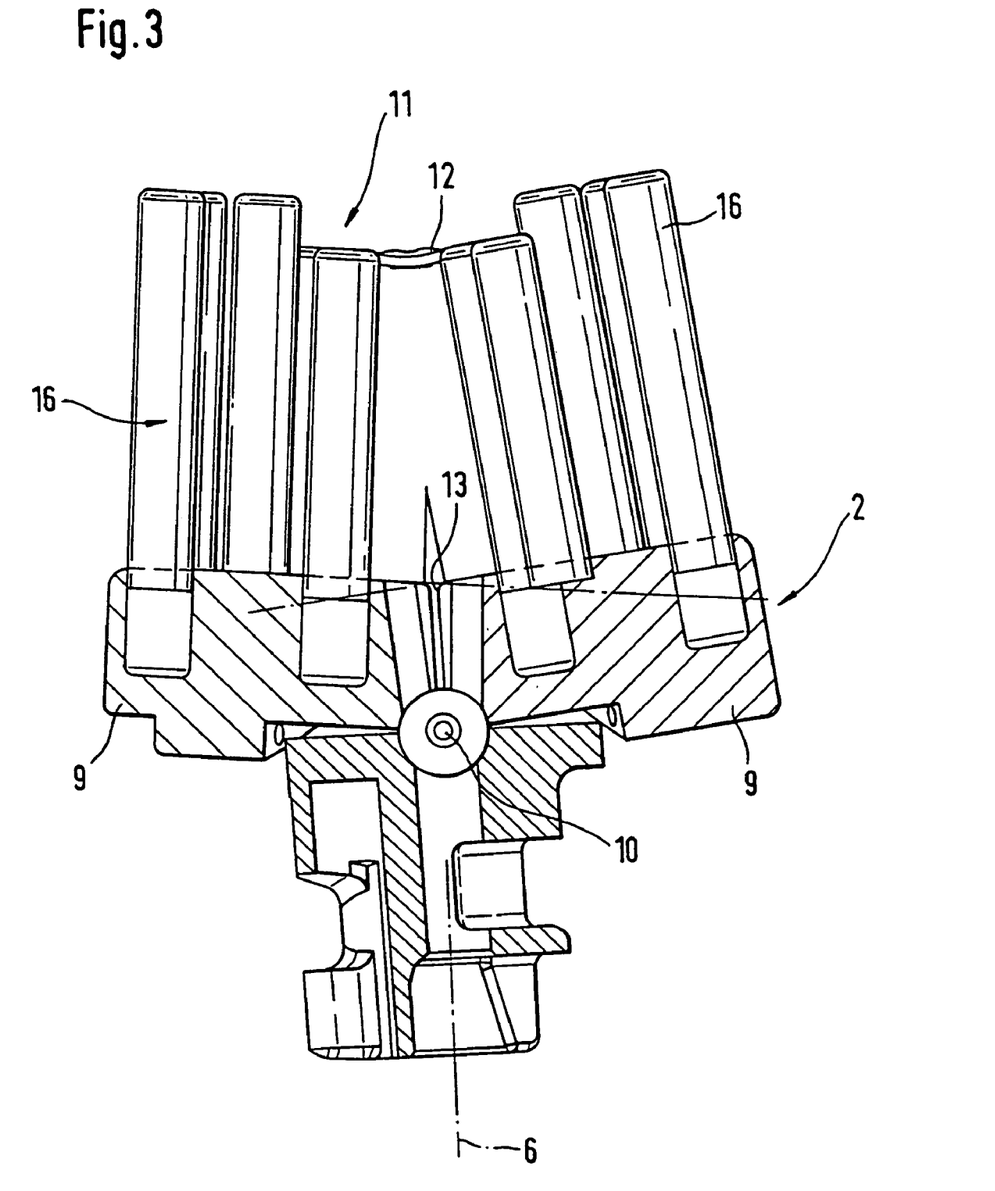
FIG. 3 is a sectional view of a bristle support having movably mounted bristle support segment according to another embodiment of the invention in which the movable bristle support segments are mounted for swivel movement about a common transverse axis.

While the two bristle support segments 9 of FIGS. 1 and 2 are adapted to swivel about separate transverse axes 10, provision may also be made for mounting the two movable bristle support segments 9 for swivel motion about a common transverse axis 10 as shown in FIG. 3. Otherwise the bristle support shown in FIG. 3 corresponds to the embodiment previously described. It shows that preferably bristles referred to as power tips sit on the movable bristle support segments 9. The radially outer bristle tufts 16 arrayed on an outer ring of bristle tufts protrude in the bristles' longitudinal direction beyond the radially inner bristle tufts as well as the bristle tufts arranged on the rigid bristle support segment 8, enabling them to better penetrate in interproximal spaces. Furthermore, the radially outer bristle tufts 16 may be of increased stiffness. This too assists in penetrating between the teeth.

The brush head 1 shown in FIGS. 4 to 7 comprises likewise an essentially disk- or plate-shaped bristle support 2 mounted for rotation on an elongate brush head support 3. Similar to the previously described embodiment, the brush head support 3 comprises a brush tube 4 and a bristle support mounting structure 5 receiving the bristle support 2 or mounting it rotatably. The bristle support 2 is adapted to be driven in the manner previously described, meaning in an oscillatory rotating manner about the axis of rotation 6 which is perpendicular to the plane of the bristle support and perpendicular to the longitudinal axis of the brush head 1. For this purpose and as described in the foregoing, a corresponding driving element and, as the case may be, a gearing may be arranged in the interior of the brush head support 3.

Figure 5:
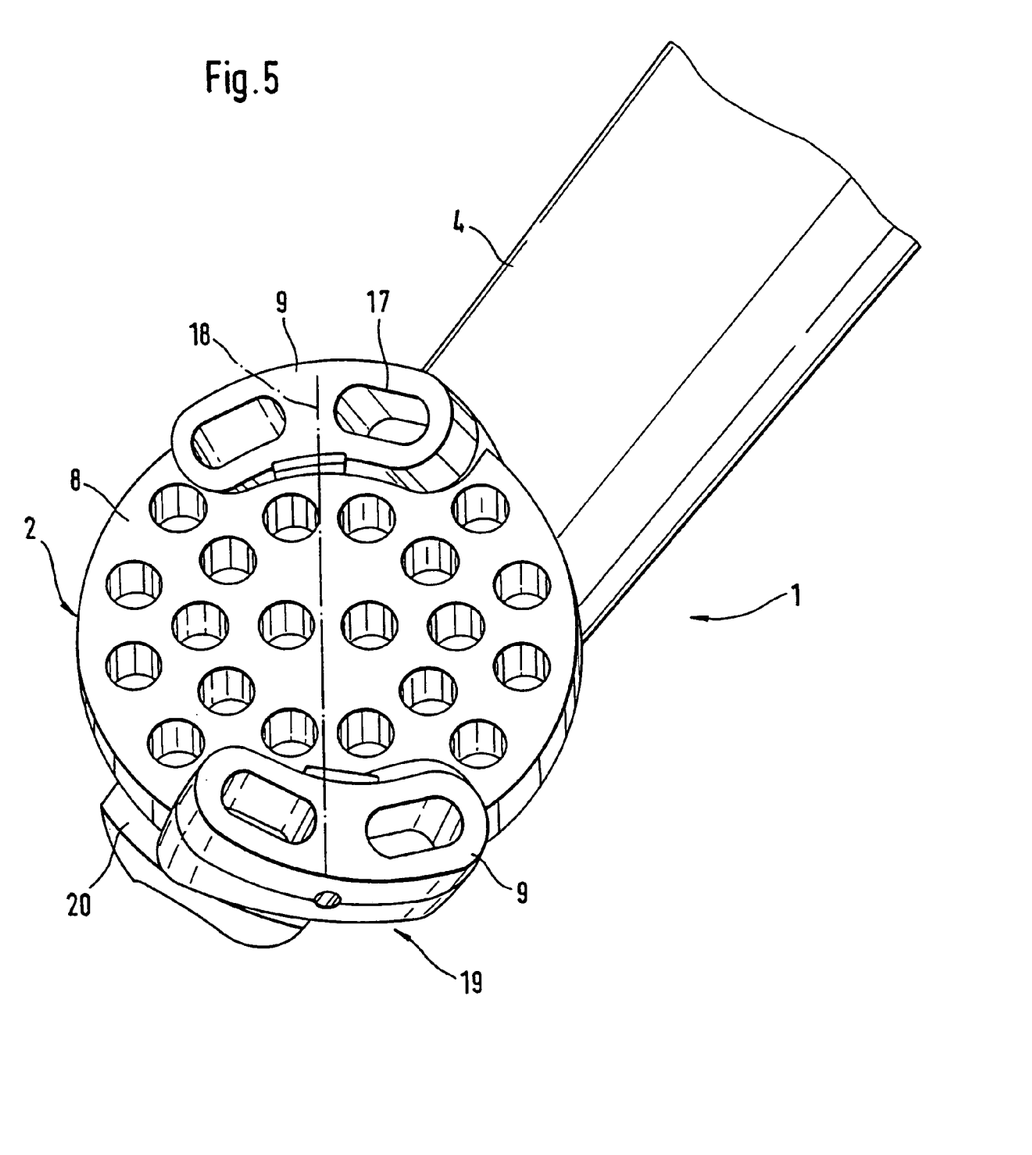
FIG. 5 is a top plan view of the brush head of FIG. 4 showing the arrangement of the movable bristle support segments.

The bristle support 2 is likewise comprised of a rigid bristle support segment 8 and two movably mounted bristle support segments 9 in diametrically opposite arrangement, which combine with the rigid bristle support segment 8 to form an essentially circular disk. As FIG. 5 shows, the movable bristle support segments 9 are arranged on the outer periphery of the bristle support 2. The bristle support segments 9 have the approximate contour of a circular ring segment forming part of the peripheral region of the bristle support 2. In the non-displaced position of the bristle support 2 shown in FIG. 7, the movable bristle support segments 9 lie roughly on the longitudinal axis of the brush head 1 which is essentially defined by the brush tube 4. From the neutral position of FIG. 7 the bristle support 2 can be oscillated rotationally in opposite directions through an arc of up to ±45°, preferably ±35°, approximately.

Each of the bristle support segments 9 has recesses 17 for receiving suitable bristle tufts. In the embodiment shown, each bristle support segment 9 accommodates two bristle tufts of longitudinal cross-section. In this embodiment in particular, the bristle tufts are likewise configured as power tips protruding in the bristles' longitudinal direction beyond the bristle tufts sitting on the fixed bristle support segment 8, and possess greater stiffness. They serve to penetrate in the interproximal spaces.

Figure 4:
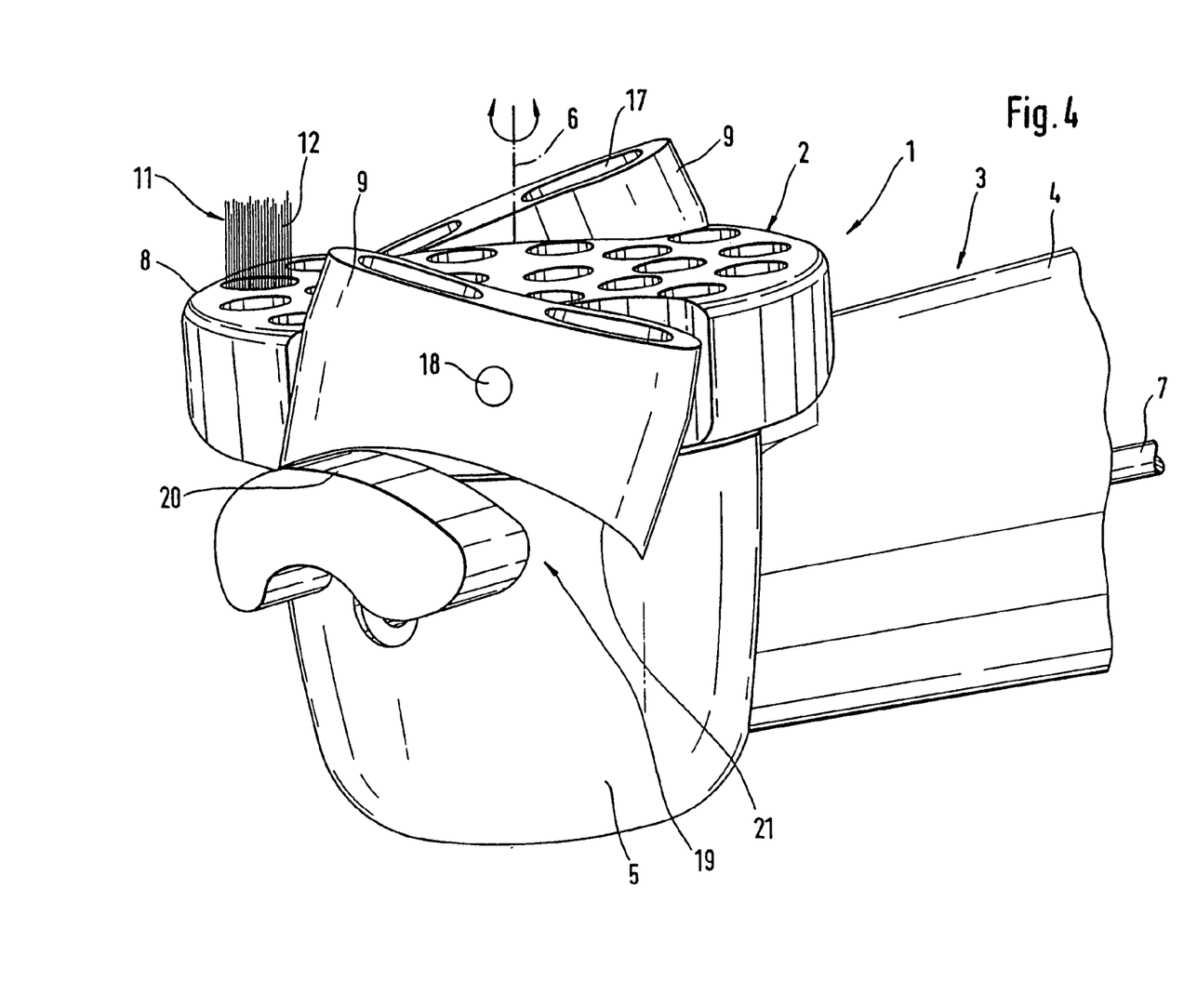
FIG. 4 is a perspective view of a brush head of another electric toothbrush, in which the bristle support adapted to be driven in an oscillatory rotating manner includes two bristle support segments mounted for swivel movement about a radial axis, the view showing a cam control of the movably mounted bristle support segments.

In contrast to the previously described embodiment, the bristle support segments 9 are adapted to swivel relative to the rigid bristle support segment 8 about a radial axis 18. The radial axis 18 extends essentially in the plane of the bristle support 2 in a direction transverse to its axis of rotation 6 and essentially through the segments of the bristle support 2 in which the movable bristle support segments 9 are provided. In the non-displaced position of the bristle support 2, the radial axis 18 extends in the longitudinal direction of the brush head 1. As FIGS. 4 and 5 show, the bristle support segments 9 are tiltable about the radial axis 18 in such a manner that the bristle tufts spaced from the radial axis 18 execute a poking motion. In particular the bristle tufts arranged on the bristle support segments 9 perform a wagging motion in the circumferential direction roughly in a plane tangential to the bristle support 2. In the non-displaced position shown in FIG. 7, the movable bristle support segments 9 lie substantially in the plane defined by the rigid bristle support segment 9.

Figure 6:
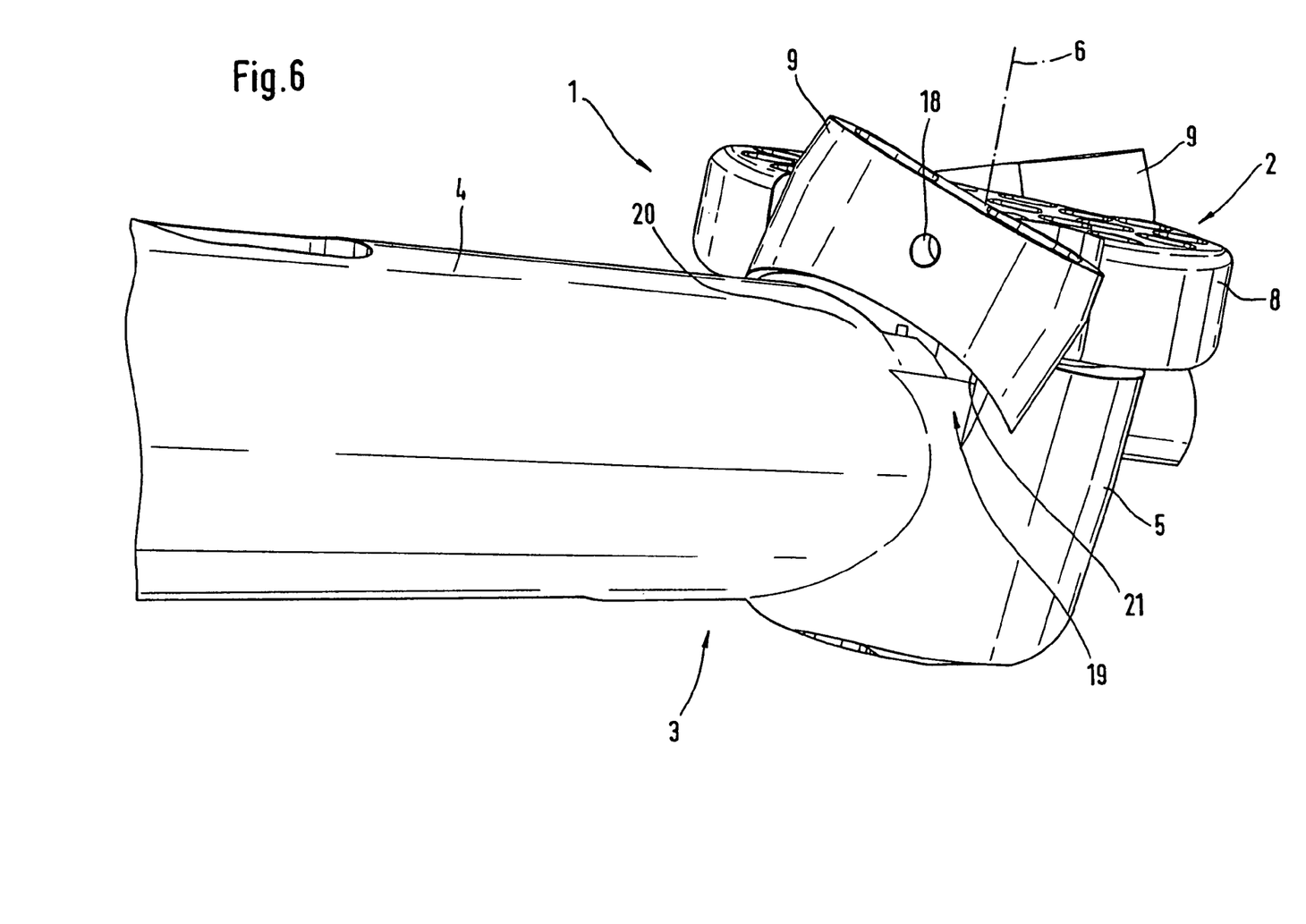
FIG. 6 is a perspective view of the brush head of the two preceding Figures, showing a brush tube and a cam control, formed in part by the brush tube, of the movable mounted bristle support segment.

The movement of the bristle support segments 9 is positively-controlled in dependence upon the rotation of the bristle support 2 about the axis of rotation 6. As driving device provision is made for a cam control 19 causing the bristle support segments 9 to swivel about the radial axis 18 during rotation of the bristle support 2 about its axis of rotation 6. As FIGS. 4 and 6 show, each of the bristle support segments 9 is associated with a cam control surface 20 arranged essentially underneath the bristle support segments 9 and formed fast with the brush head support. The cam control surface 20 associated with the bristle support segment 9 on the side close to the handpiece is formed by the surface of the brush tube 4. The cam control surface 20 associated with the opposite, frontal bristle support segment 9 is formed by a frontal projection on the bristle support mounting structure 5 (cf. FIG. 4). Each of the two cam control surfaces 20 is curved in convex shape.

Figure 7:
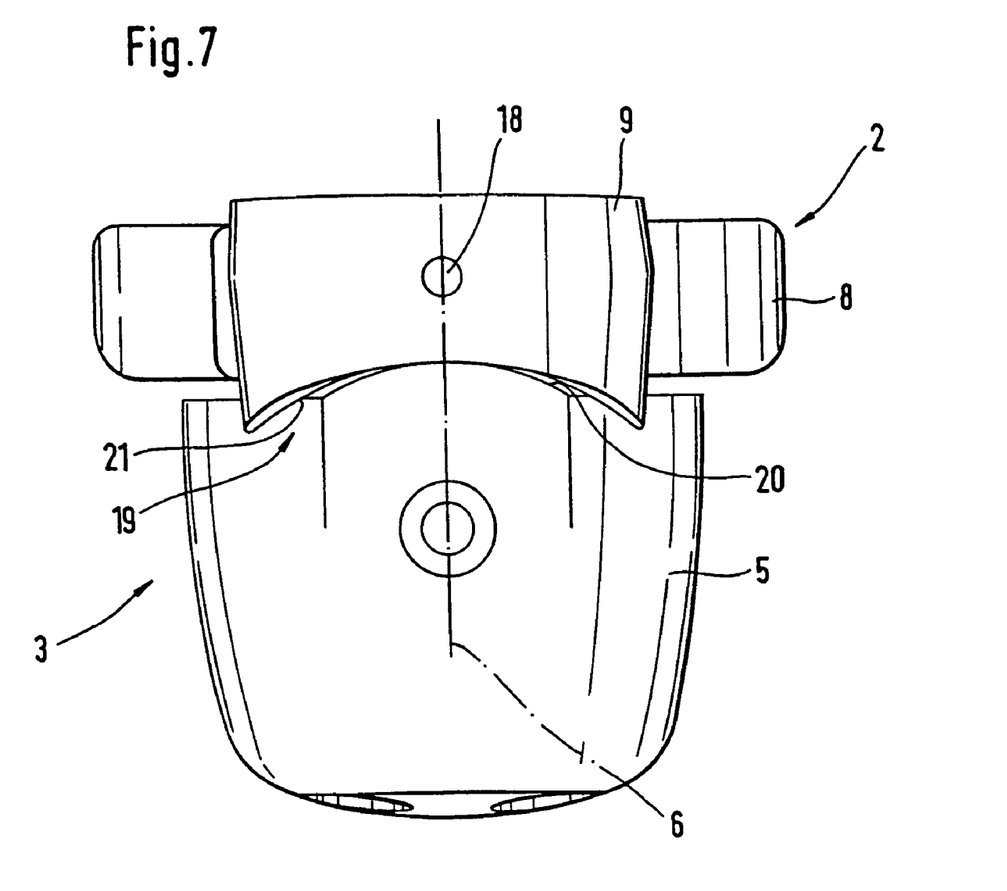
FIG. 7 is a front view of the brush head of the preceding FIGS. 4 to 6, showing the movably mounted bristle support segments in their non-displaced, neutral position.

The bristle support segments 9 have on their underside close to the brush tube 4 a respective engagement element 21 for engagement, in particular sliding engagement, with the respective cam control surface 20. In the embodiment shown, the engagement element is the underside of the bristle support segments 9 itself, which is curved in convex shape in such manner as to be in intimate engagement with the cam control surface (FIG. 7). Conveniently, the bristle support segment 9 extends in the circumferential direction of the bristle support 2 over a greater length than the cam control surface 20 (FIG. 7). In the embodiment of FIGS. 4 to 7, the cam control 19 is configured such that in the neutral position of the bristle support 2, that is, when it is in a mid-position of its oscillating rotation shown in FIG. 7, the bristle support segments 9 are non-displaced. By contrast, the maximum stroke motion, that is, the maximum amount of displacement of the bristle support segments 9 about the radial axis 18, takes place in the maximum rotated position of the bristle support 2. As this occurs, the two bristle support segments 9 are turned in opposing directions (FIG. 4). Considering however that the two bristle support segments 9 carry bristle tufts on either side of the radial axis 18, a bristle tuft stroke motion results on both bristle support segments 9 in the same timed sequence, that is, the power tips on opposed sides of the bristle support 2 are raised at the same time to poke into the interproximal spaces.

The invention claimed is:

1. A brush head attachment for an electric toothbrush, the brush head comprising
   a brush head support including a support mounting structure;
   a bristle support carrying an array of bristles and mounted for movement on the brush head support, said bristle support comprising multiple bristle support segments movable relative to each other, the multiple bristle support segments including a first support segment that rotates about a first axis, and a second support segment that both rotates about the first axis and selectively swivels about a second axis, and
   driving elements that change the position of the movable bristle support segments relative to each other as a function of a position of said bristle support,
   wherein said driving elements are provided on the brush head support and on at least one of the bristle support segments and wherein said driving elements comprise a cam control surface and an engagement element cooperating with the cam control surface.

2. The brush head of claim 1 wherein the bristle support is mounted for rotation about the first axis, and wherein the cam control surface is arranged on an arc about the first axis.

3. The brush head of claim 2 wherein the bristle support is adapted to be driven in an oscillatory rotational motion.

4. The brush head of claim 2 wherein the first axis lies in a direction transverse to a longitudinal axis of the brush head.

5. The brush head of claim 2 wherein the cam control surface is formed on the brush head support.

6. The brush head of claim 1 wherein multiple bristle support segments are adapted to be driven in dependence upon rotary position of the bristle support, with the cam control surface including several sections, one of which sections being associated with a corresponding one of the bristle support segments.

7. The brush head of claim 6 wherein the bristle support segments adapted to be driven in dependence upon the rotary position of the bristle support include one pair of bristle support segments arranged at diametrically opposite sides of the bristle support.

8. The brush head of claim 1 wherein the cam control surface and the engagement element cooperating therewith are always in relative engagement and act in opposed directions of movement.

9. The brush head of claim 1 wherein the cam control surface and the engagement element cooperating therewith are disengageable from each other and maintained in relative engagement by reaction forces developing while brushing the teeth.

10. The brush head of claim 1 wherein construction of the driving elements and mounting of the movable bristle support segments are such that upon rotation of the bristle support about the first axis, at least some of said bristle support segments execute a poking motion in a direction of the first axis.

11. The brush head of claim 1 wherein the bristle support has a neutral position from which the bristle support is drivable in oscillatory manner in opposite directions, and wherein the cam control surface is configured such that a bristle support segment driven by the cam control surface obtains a maximum stroke position in the neutral position of the bristle support while occupying a minimum stroke position when displacement of the bristle support from its neutral position is at a maximum.

12. The brush head of claim 1 wherein the bristle support has a neutral position from which the bristle support is drivable in oscillatory manner in opposite directions, and wherein the cam control surface is configured such that a bristle support segment driven by the cam control surface obtains a minimum stroke position in the neutral position of the bristle support while occupying a maximum stroke position when displacement of the bristle support from its neutral position is at a maximum.

13. The brush head of claim 1 wherein multiple ones of the bristle support segments are raised by corresponding cam control surfaces according to a given timed sequence.

14. The brush head of claim 1 wherein the second axis is a swivel axis that extends in a radial direction, such that bristles on the bristle support segment mounted for swivel movement about the swivel axis swivel in a plane tangential to a circumferential direction of the bristle support.

15. The brush head of claim 1 wherein the second axis is a swivel axis that extends in a direction transverse to the bristle support segment mounted for swivel movement about a swivel axis, such that bristles on that bristle support segment swivel in a direction parallel to a radial plane containing an axis of rotation of the bristle support.

16. The brush head of claim 1 wherein the cam control surface comprises a surface of the brush head support.

17. The brush head of claim 1 wherein the cam control surface is formed directly by a section of a bristle support mounting structure of the brush head support.

18. The brush head of claim 1 wherein the cam control surface is formed by an element separate from, and fixedly connected with, the brush head support.

19. The brush head of claim 1 wherein the engagement element forms a curved engagement surface that is curved in a same direction as, and with about the same curvature radius as, the cam control surface.

20. The brush head of claim 1 wherein the cam control surface includes at least two concave depressions and a protuberance connecting said depressions, and wherein the engagement element forms a curved engagement surface whose curvature corresponds approximately to one of said depressions.

21. The brush head of claim 1 wherein the driving elements and the movable bristle support segments lie approximately along a longitudinal axis of the brush head when the bristle support is in a non-displaced position.

22. The brush head of claim 1 wherein each bristle support segment that cooperates with the cam control surface includes bristles that differ in kind from other bristles of the brush head.

23. The brush head of claim 22 wherein each bristle support segment that cooperates with the cam control surface carries bristles that protrude, in a longitudinal direction of the bristles, beyond other bristles of the brush head.

24. The brush head of claim 22 wherein each bristle support segment that cooperates with the cam control surface carries bristles of greater stiffness than other bristles of the brush head.

25. The brush head of claim 1 wherein each bristle support segment that cooperates with the cam control surface forms a radially outer peripheral portion of the bristle support and carries radially outer bristles.

26. The brush head of claim 1 wherein the bristle support includes at least one rigid, immovable bristle support segment having bristle tufts secured thereto.

27. The brush head of claim 1 adapted to be releasably attached to a handpiece of an electric toothbrush.

28. The brush head of claim 1 wherein the first axis is perpendicular to the second axis.

29. A toothbrush comprising
a handpiece;
a motor disposed within the handpiece; and
a brush head comprising
   a brush head support;
   a bristle support connected to the motor, the bristle support carrying an array of bristles and mounted for movement on the brush head support, said bristle support comprising multiple bristle support segments movable relative to each other, the multiple bristle support segments including a first support segment that rotates about a first axis, and a second support segment that both rotates about the first axis and selectively swivels about a second axis; and
   driving elements that change the position of the movable bristle support segments relative to each other as a function of a position of said bristle support,
   wherein said driving elements are provided on the brush head support and on at least one of the bristle support segments and wherein said driving elements comprise a cam control surface and an engagement element cooperating with the cam control surface.

* * * * *